US007016464B2

(12) United States Patent
Ritt et al.

(10) Patent No.: US 7,016,464 B2
(45) Date of Patent: Mar. 21, 2006

(54) RADIOGRAPHIC IMAGING SYSTEM AND METHOD

(75) Inventors: Daniel M. Ritt, Colorado Springs, CO (US); Matthew L. Whitaker, Colorado Springs, CO (US)

(73) Assignee: Radiological Imaging Technology, Inc., Colorado Springs, CO (US)

( * ) Notice: Subject to any disclaimer, the term of this patent is extended or adjusted under 35 U.S.C. 154(b) by 0 days.

(21) Appl. No.: 11/126,806

(22) Filed: May 11, 2005

(65) Prior Publication Data

US 2005/0213704 A1    Sep. 29, 2005

Related U.S. Application Data

(63) Continuation of application No. 10/688,130, filed on Oct. 17, 2003, now Pat. No. 6,934,358.

(60) Provisional application No. 60/491,385, filed on Jul. 31, 2003.

(51) Int. Cl.
   *G01N 23/083* (2006.01)

(52) U.S. Cl. ............................. 378/62; 378/4; 378/901
(58) Field of Classification Search .................. 378/4, 378/8, 15, 19, 62, 98, 901
See application file for complete search history.

(56) References Cited

U.S. PATENT DOCUMENTS

| 4,407,299 | A  | * | 10/1983 | Culver ........................ 600/544 |
| 4,408,616 | A  | * | 10/1983 | Duffy et al. ................. 600/544 |
| 4,421,122 | A  | * | 12/1983 | Duffy .......................... 600/544 |
| RE34,015  | E  | * | 8/1992  | Duffy .......................... 600/544 |
| 5,442,674 | A  |   | 8/1995  | Picard et al. |
| 2002/0048347 | A1 | | 4/2002 | Saito |

OTHER PUBLICATIONS

PCT International Search Report, 3 pages.

* cited by examiner

*Primary Examiner*—David V Bruce
(74) *Attorney, Agent, or Firm*—Rader, Fishman & Grauer PLLC (57) ABSTRACT

The invention relates generally to systems and methods for processing radiographic and other medical-related images (collectively "imaging system" or simply the "system"). More specifically, the invention relates to a system for associating particular calibration information with a particular radiographic image. Calibrated images processed by the system can be created from radiographic images and calibration information associated with the radiographic images. In many embodiments, the system includes a user interface that automatically configures itself in accordance with the calibration information embedded with the radiographic image. The system can include a user interface configured to obtain the calibration from the data object.

16 Claims, 6 Drawing Sheets

RADIOGRAPHIC IMAGING SYSTEM AND METHOD

RELATED APPLICATIONS

This application is a continuation of application Ser. No. 10/688,130, filed on Oct. 17, 2003 now U.S. Pat. No. 6,934,358. Application Ser. No. 10/688,130 claims priority from provisional application 60/491,385, filed on Jul. 31, 2003. Each of the foregoing applications is hereby incorporated herein by reference in its entirety.

BACKGROUND OF THE INVENTION

The present invention relates to systems and methods for processing radiographic and other medical-related images (collectively "imaging system" or simply the "system"). More specifically, the system associates radiographic images with calibration information relating to those radiographic images.

In typical medical-imaging applications, a large number of images can be generated each day. For each generated image, raw image data is typically recorded in arbitrary units that are related to the acquisition process, the device that acquired the image, or some other process that can vary from user to user. The acquired image data is then typically stored in one or more computer-readable files. If multiple files are used to represent the image data, it is then necessary to associate those various files with each other to prevent the files from being separated. Separation of such information would substantially impair the usefulness of the captured images. To this end, related image files often share a basic file name and have different file extensions. However, different users may use different conventions for relating files and images with each other.

Various medical personnel may need to view or otherwise use the image data at different times in wide variety of formats. Image files that contain the raw image data in arbitrary units are usually not useful to the medical personnel who need to view the medical images. In order to make the image files useful, the raw image data is converted to other units or formats that are typical in the field of medical imaging. Once converted to a useful format, medical personnel are able to use the image data as needed. In radiation oncology, raw image data is often converted to units such as Optical Density (OD) units (a logarithmic scale representing the amount of transmission through a film) or dosage units (Gray (GY) is the international unit for dosage).

To convert raw image data into useful units, a calibration is performed on the raw image data. To perform such a calibration, calibration information that is specific to the raw image data must be used because the calibration information is typically applicable only to specific imaging conditions. For example, in radiation oncology, the calibration information may be specific to acquisition-related parameters such as the maximum and minimum dose, the type of film used to acquire the raw image data, a radiation delivery medium (e.g., photons or electrons), or any other condition or combination of conditions that relate to image acquisition. Therefore, specific calibration information is typically created and used to convert an image to more useful formats.

Acquired raw image data is not immediately converted to usable units upon acquisition because it is often desirable that the raw image data be preserved for use in future applications or conversions. A future user of the information may desire a different format, and that different format may be best generated from the initial raw image data. For instance, preserved raw image data can be converted to a newly developed format. Updates can also be made to the raw image data for inclusion in future conversions. Further, preserved raw image data can be repeatedly calibrated to multiple types of formats. In short, medical personnel enjoy more flexibility when raw image data is preserved for conversions. Therefore, it would be desirable for medical-imaging applications to maintain the raw image data for each acquired image and convert the raw image data to useful formats as it is needed by medical personnel.

In order to preserve the raw image data for subsequent conversion to useful formats, conventional medical-imaging applications typically create and use calibration files to represent the specific calibration information that is used to convert the raw image data. However, unlike the image files, a calibration file in a conventional medical-imaging application is not automatically associated with a specific image file because the calibration file is configured to apply to several images, classes of images, certain patients' images, or specific machine parameters. Further, calibration files are frequently used for an extended period of time to convert images with specific imaging conditions. As a result, a calibration file usually does not share a basic file name or any other type of easily recognized naming convention with a particular image file. In other words, medical personnel must keep track of which calibration files are associated with specific image files.

The process of keeping track of calibration files and image files is a daunting administrative chore to medical personnel and facilities that deal with large numbers of medical images. Medical personnel often encounter problems associated with keeping track of numerous calibration and image files. Not only must personnel remember which calibration file to use for each image file, they also must remember where the calibration file is located. This is especially burdensome on a person's memory when an image taken months or years ago must be calibrated for viewing. Even though the image file is available, the appropriate calibration file may have been misplaced or overwritten. Thus, the problem of relying on personnel to manually track and maintain calibration files is exacerbated by large numbers of files that accumulate over time. Moreover, a change in personnel could result in the loss of any knowledge as to the location or the association of calibration files in relation to image files.

Further complicating the problems associated with tracking calibrations and image files information, calibration files are often updated during their lifetime. In conventional medical-imaging applications, updates to a calibration file have global consequences. When a calibration file is modified in order to convert a new image into usable units, that calibration file may no longer accurately convert older images that it was once configured to convert. If no copy of the previous version of the calibration file was maintained, the calibration information for the older images is lost. Moreover, if the updated calibration file is used to convert one of the older images, the older image will be calibrated incorrectly, and conventional medical-imaging applications will not detect such an error. The erroneous conversion may result in a patient suffering a medical misdiagnosis, a misadministration, or a mistreatment. Therefore, it is desirable for a medical-imaging application to associate calibration information with image data in a more efficient and automated manner, involving less manual administration by users. Personnel who need to be focusing on helping patients should not be overly burdened with maintaining an information technology necessary for accessing configuration data and associated images in a meaningful way.

Conventional medical imaging applications do not provide robust and flexible interfaces. Specifically, the conventional applications' interfaces limit a user's ability to manage and convert image files according to calibration files. The conventional applications offer only traditional file storage systems to track image files and related calibration files. Moreover, conventional interfaces require user intervention to calibrate an image file for display. Conventional interfaces also fail to automatically configure their operations according to image calibrations. It would be desirable for a medical-imaging application interface to provide flexibility, convenience, proactive, and robust functionality for managing and using image files and calibration data.

SUMMARY OF THE INVENTION

The invention relates to a system or method for processing radiographic and other medical-related images (collectively "imaging system" or simply the "system"). More specifically, the system performs the functionality of associating images with calibration information. A data object processed by the system can include a radiographic image and one or more calibration attributes associated with the radiographic image. The system can include an interface that is configured to obtain the calibration from the data object. The interface of the system can proactively configure itself in accordance with the calibration attributes associated with a particular image.

DETAILED DESCRIPTION OF THE DRAWINGS

Certain embodiments of the present systems and methods will now be described, by way of examples, with reference to the accompanying drawings, in which.

DETAILED DESCRIPTION

I. Introduction of Elements and Definitions

The invention relates to the processing radiographic and other medical-related images (collectively "imaging system" or simply "the system"). More specifically, the system provides for associating a particular image with one or more calibration attributes related to the particular image. The system can also be referred to as a radiographic imaging system, a radiographic system, a radiological imaging system, or a radiological system.

The imaging system can be used in a variety of different medical-related contexts, including radiation oncology and any other processing of medical-related images. The system can be implemented in a wide variety of different devices and hardware configurations. Similarly, a wide variety of different interfaces, software applications, operating systems, computer hardware, and peripheral components may be incorporated into or interface with the system. Numerous combinations and environments can utilize one or more different embodiments of the system.

In the following description, for purposes of explanation, numerous specific details are set forth in order to provide a thorough understanding of the system. It will be apparent, however, to one skilled in the art that the present methods and systems may be practiced without all of the specific details of the disclosed examples. Reference in the specification to "one embodiment," "an embodiment," or "an exemplary embodiment" means that a particular feature, structure, or characteristic described in connection with the embodiment is included in at least one embodiment. The phrases "in one embodiment" and "in an exemplary embodiment" appear in various places in the specification and are not necessarily all referring to the same embodiment.

Figure 1:
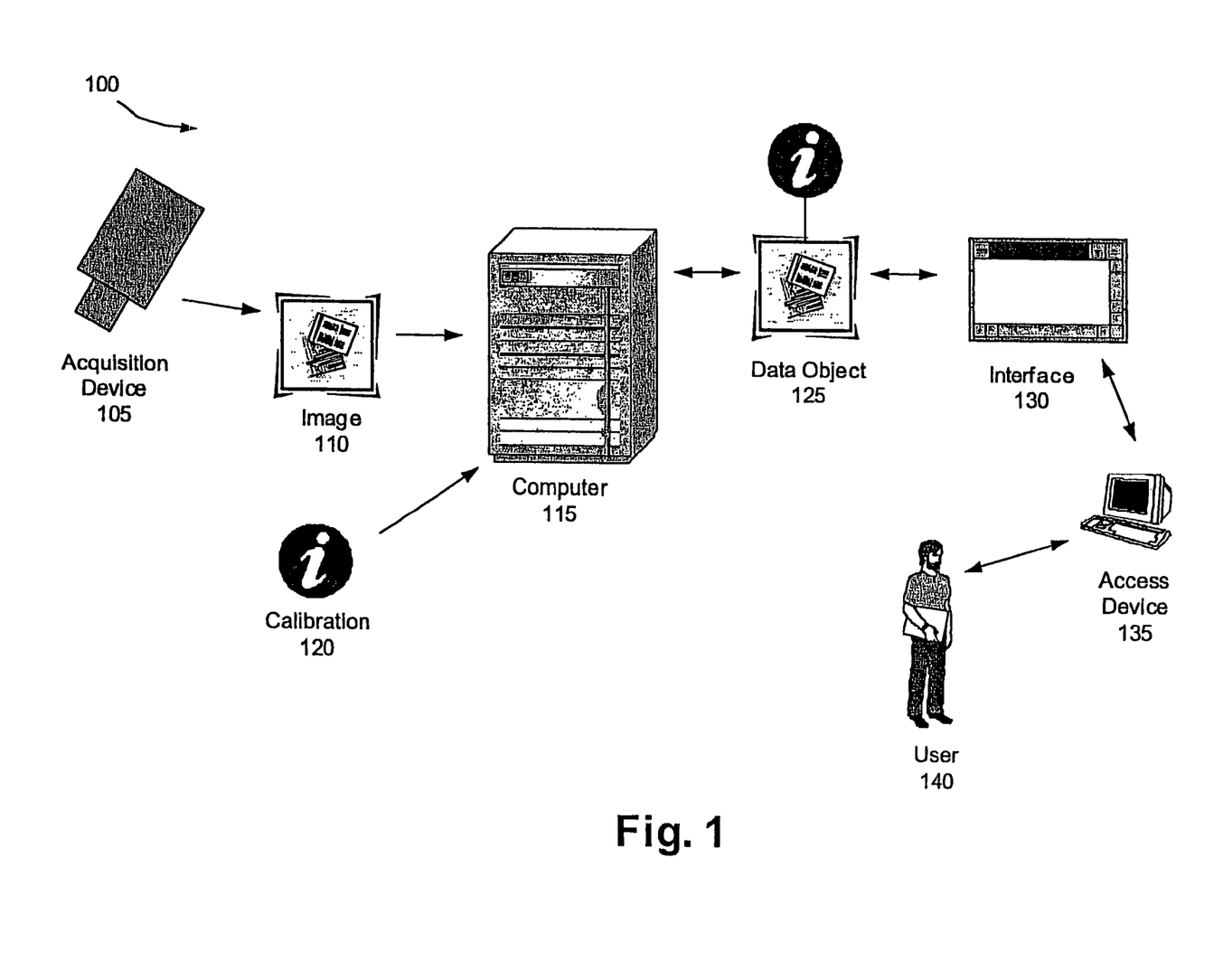
FIG. 1 is an environmental diagram illustrating an example of a system for processing medical-related images.

Referring now to the drawings, FIG. 1 is a diagram illustrating an example of a system 100 for processing medical-related images. An acquisition device 105 is configured to acquire or generate an image 110. The acquisition device 105 is communicatively coupled to a computer 115 and can communicate the image 110 to the computer 115. The computer 115 is configured to receive the image 110 and one or more calibrations 120 relating to that image. The image 100 can be associated with numerous different calibrations 120, including mutually exclusive or contradictory calibrations 120. The computer 115 can generate a data object 125 based on the image 110 and the calibration(s) 120. The data object 125 can be accessed through an interface 130. An access device 135 can be used by a user 140 to access and use the interface 130. For illustrative purposes only, FIG. 1 shows a camera to represent an acquisition device 105, a computer tower to represent a computer 115, a graphical user interface (GUI) to represent an interface 130, a computer terminal to represent an access device 135, and a human being to represent a user 140.

Although FIG. 1 shows one acquisition device 105, one image 110, one computer 115, one calibration 120, one data object 125, one interface 130, one access device 135, and one user 140 for illustrative purposes, it will be clear to one of ordinary skill in the art that the system 100 can include more than one of each element, including a wide variety of different combinations of devices. In an exemplary embodiment, the computer 115 interfaces with a number of other computers 115. The elements of the exemplary system 100 shown in FIG. 1 will now be discussed in further detail below.

A. Acquisition Device

The acquisition device 105 can be any device or application capable of acquiring, generating, or otherwise obtaining an image 110, including but not limited to a camera, a scanner, a digital device, a computer, a magnetic resonance imaging ("MRI") device, a computerized axial tomography ("CAT" or "CT") device, an X-ray device, an ultrasound device, a light-based sensor, a non-light-based sensor, and a software application. The acquisition device 105 may be configured to acquire or generate an image 110 that is representative of medical-related information. The acquisition device 105 can apply or use a specific unit of measurement in generating an image 110, and that unit of measurement can be related to a parameter or a setting of the acquisition device 105, the acquisition setup, the acquisition process, or the captured information.

The acquisition device 105 can generate calibration information relating to the generation of an image 110. Some examples of calibration information are discussed in greater detail below. In some embodiments, the acquisition device 105 generates a file or a group of files to represent the acquired image 110. In some embodiments, the acquisition device 105 generates a file or multiple files to represent calibration information that is related to an acquired image 110. In various embodiment, the acquisition device 105 can be configured to generate a calibration file and a related image file in a simultaneous or substantially simultaneous manner.

Different embodiments can involve different configurations of acquisition devices 105 and images 110. For example, some acquisition devices 105 use photons in the acquisition of the image 110, while other acquisition devices 105 may use electrons to generate the image 110. Some acquisitions devices 105 may be configured to user both electrons and photons to capture images 110, while still other acquisition devices 105 can be configured to deliver doses of radiation by either electrons or photons. In many different embodiments, the acquisition device 105 can be configured to communicate, transmit, or otherwise share the image 110 and calibration information 120 with another element within the system 100, such as the computer 115.

B. Image

The image 110 can be any representation that can be read, stored, modified, deleted, or otherwise acted upon by the computer 115, including but not limited a graphical representation, a data representation, or various combinations of graphical and/or data representations. The image 110 may be included in or represented by a data object 125, a group of data objects, a file, a group of files, an array, a group of arrays, various data structures, or any other representation that can be processed by the computer 115. The representations can involve two-dimensional, three-dimensional, or even greater than three-dimensional information. The image 110 can be represented in any unit of measurement, including a unit of measure that is associated with the acquisition or generation of the image 110. The image 110 may be any medically related image, including but not limited to a radiographic image, a radiological image, an X-ray image, an MRI image, a CT image, and ultrasound image, and the like. In many embodiments, the image 110 is a radiographic image.

The image 110 can be initially acquired or generated in a wide variety of ways. The image 110 may be generated, acquired, or imported by the system 100. In many embodiments, the image 110 is acquired through the use of a light-based sensor, such as a camera. In other embodiments, the image 110 is generated by the use of a non-light based sensor. An ultrasound image is an example of an image 110 generated through the use of a non-light based sensor. In many embodiments, the image 110 is acquired or generated by the acquisition device 105. In some embodiments, the image 110 is a digital image, or an image that can be converted into a digital image. The image 110 can be imported or otherwise received from any source of computer-readable information.

C. Computer

The computer 115 is any device or combination of devices that allows the processing or functionality of the system 100 to be performed. The computer 115 may be a general purpose computer capable of running a wide variety of different software applications or a specialized device limited to particular embedded functions. In some embodiments, the computer 115 is the same device as the access device 135. In other embodiments, the computer 115 is a network of computers 115 accessed by the access device 135. The system 100 can incorporate a wide variety of different information technology architectures. The computer 115 can receive, incorporate, store, and process information that may relate to operations of the imaging system 100. The computer 115 may include any type, number, form, or configuration of processors, system memory, computer-readable mediums, software applications, interfaces, peripheral devices, and operating systems. In many embodiments, the computer 115 is a server and the access device 135 is a client device accessing the server.

Many of the processing elements of the system 100 exist as representations within the computer 115. Calibrations 120 and images 110 are examples of processing elements existing as representations within the computer 115. An image 110 may include various reference points such as calibration points, and those reference points can exist as representations within the computer 115. The computer 115 is capable of storing, accessing, creating, updating, deleting, and otherwise processing the representations of elements contained within the system 100. The computer 115 may contain memory and other computer-readable mediums that can be used to store, organize, or otherwise process the representations. The representations can include but are not limited to data objects 125.

The computer 115 can perform the processing necessary and helpful for associating representations of images 110 and calibrations 120. The computer 115 is capable of processing images 110 and calibrations 120, including the functionality of associating the appropriate calibration information 120 with the appropriate image 110. The computer 115 may perform such associations automatically at the time at which the image 110 is acquired or imported. The computer 115 can also associate calibration information 120 and an image 110 at other times, including in response to a user 140 initiated instruction that is received long after the initial capturing of the image 110. The association of calibration information 120 and images 110 will be discussed in detail below.

D. Calibration

The calibration 120 can be any representation that can be read, processed, or acted upon by the computer 115, including but not limited to a representation of information for configuring, converting, or calibrating an image 110. The calibration 120 can be included in or represented by any object readable by the computer 115, including but not limited to one or more data objects 135. The calibration 120 may include various reference points, calibration points, calibration information, configuration data, coefficients, parameters related to an image 110, equations, algorithms, or any other data useful for configuring an image 110 (collectively a "calibration" 120 or "calibration information" 120). In many embodiments, the calibration 120 is calibration data included in a file or group of files. In some embodiments, the calibration 120 includes information that can identify calibration data that is represented by a different data structure. For example, the calibration information included within the calibration 120 may include a pointer to another representation of calibration data.

A calibration 120 can include any information for converting an image 110 to a specific format or unit of measurement. Further, a calibration 120 may include information for converting an image 110 to any one of a number of formats or units of measurement. In some embodiments, the calibration 120 includes information for converting an image 110 to an Optical Density (OD) unit. In other embodiments, the calibration 120 includes information for converting an image 110 to a dosage unit such as a Gray (Gy). In many embodiments, the calibration 120 includes information for potentially converting an image 110 to both a dosage unit and an Optical Density (OD) unit.

The calibration 120 can be generated automatically by the system 100 or can be generated in response to a user 140 instruction. The user 140 may create, add, delete, change, or otherwise act upon a calibration 120 through the interface 130. This functionality will be discussed in more detail in relation to the interface 130 below.

The calibration 120 can be applied to an image 110 in order to convert, calibrate, or otherwise configure the image 110 according to the calibration 120. In some embodiments, the computer 115 and the interface 130 apply the calibration 120 to the image 110. In many embodiments, the system 100 generates a calibrated image (which can be referred to as a "calibration image") based on application of a calibration 120 to an image 110.

The calibration 120 can be associated with an image 110. The computer 115 or the interface 130 can perform the functionality of associating the calibration 120 with the image 110. The association can include but is not limited to inserting the image 110 and the calibration 120 into a data object 125 such as a file, inserting the image 110 and the calibration 120 into a group of associated files or data objects 125, embedding the calibration 120 into the image 110, embedding the calibration 120 in a file or data object that is associated with the image 110, or any other way of forming a relationship between the image 110 and the calibration 120 that can be recognized by the computer 115 or by the interface 130. In many embodiments, the calibration 120 is embedded in a file or other type of data object 125 that includes the image 110. In some embodiments, the calibration 120 is embedded in a header that is associated with a file that includes the image 110. The header may be included in the file, or the header may be a separate file that is associated with the file that is representative of the image 110. In some header embodiments, the header file is associated with the image file by a common part of a filename and a distinguishable part of the filename such as a file extension, prefix, or suffix. Multiple calibrations 120 can be associated with one image 110 in any of the ways described above.

The system 100 can generate both lasting and temporary associations between a calibration 120 and an image 110. A temporary association is any association that does not remain intact. Usually, a user 140 of the system must intervene to associate an image 110 and a calibration 120 have only been temporarily association previously. If a calibration 120 has been lastingly or permanently associated with an image 110, then no human intervention is needed to apply the calibration 120 to the associated image 110. Similar to the discussion above, a lasting association can include but is not limited to inserting the image 110 and the calibration 120 into a data object or file, inserting the image 110 and the calibration 120 into a group of associated files or data objects, embedding the calibration 120 in the image 110, embedding the calibration 120 in a file or data object that is associated with the image 110, or any other way of forming a relationship between the image 110 and the calibration 120 that can be recognized by the computer 115 or by the interface 130.

E. Data Object

The data object 125 can be any representation of an association between an image 110 and a calibration 120 that can be read, processed, or acted upon by the computer 115 or the interface 130. The data object 125 may include but is not limited to a file, a group of files, and any other data structure or group of data structures capable of associating a calibration 120 with an image 110. In many embodiments, data objects 125 are some type of file. In some embodiments, the format and organizational structure of the files are predefined, while in other embodiments, the format and organization structure of the files can be set dynamically. Similar to the discussion above, the data object 125 can include a representation of the image 110 and a representation of the calibration 120. In many embodiments, the data object 125 includes a file or a group of files representative of the image 110 and a calibration 120 that is embedded in the file or group of files representative of the image 110.

In some embodiments, the data object 125 includes a file header, which header contains the calibration 120 that is associated with the image 110 of the data object 125. The file header can be part of a file that contains the image 110 or a separate file that is associated with the image 110.

The data object 125 may include information associated with a specific medical patient or a specific medical treatment. The data object 125 can represent a patient dossier. In one embodiment, the data object 125 includes multiple files that are associated with a specific medical patient. The files can include an image 110 and a calibration 120.

The data object 125 can be accessed and processed by the computer 115 and the interface 130. The data object 125 is configured such that the computer 115 or the interface 130 can automatically apply the data object's calibration 120 to the data object's image 110. In some embodiments, no user intervention is required to apply the calibration 120 to the image 110 of the data object 125. The computer 115 can use the data object 125 to convert, calibrate, or otherwise configure an image 110 according to an associated calibration 120. The data object 125 is configured to allow such instructions to be performed automatically or without human intervention.

The data object 125 can be transmitted from the computer 115 to another computer 115 or a group of computers 115. Any other computer 115 can access and process the data object 125 in order to apply the calibration 120 to the associated image 110. The computer 115 need only receive the data object 125 or embedded file to apply the calibration 120 to the image 110 automatically or without human intervention. The data object 125 is transportable and useful between computers 115 that operate the interface 130. The data object 125 may be transmitted to an archival or other type of storage device for later accessing and processing by any computer 115 operating the interface 130. In one embodiment, an image 110 is acquired at a first location and a representation of the image as calibrated is provided for viewing by a second user 140 at a second location that is remote to the first location. Such remote locations can vary widely in their relative distance to the first or non-remote locations.

F. Interface

The data object 125 can be communicated to or accessed by an interface 130. The interface 130 can be any information technology layer or combination of information technology layers that can access or act upon the data object 125, a representation of an image 110, or a representation of a calibration 120 that is included in the computer 115.

Examples of interfaces 125 include but are not limited to: a software application, a group of software applications, a GUI, an intranet, an extranet, the Internet, a local area network ("LAN"), a wide area network ("WAN"), a network, and the like. The interface 130 is any application of logic that allows a user 140 and the computer 115 to communicate in regards to an image 110, a calibration 120, or any function related to the image 110 or the calibration 120. In many embodiments, the interface 130 is some type of GUI or web page that provides a graphical means for the user 140 to interact with the system 100.

The interface 130 can be programmed or configured to act upon the data object 125, the image 110, or the calibration 120 in a wide variety of ways. The interface 130 can instruct the computer 115 to receive, add, delete, move, copy, rename, modify, or otherwise affect any representation of an image 110 or a calibration 120. The interface 130 can facilitate or perform an association of a calibration 120 with an image, including a temporary association or a lasting association. The interface 130 can also facilitate or perform a disassociation of a calibration 120 and a corresponding image 110. The interface 130 can convert, calibrate, or otherwise configure an image 110 in accordance with a calibration 120. The calibration 120 to be applied to an image 110 can be determined from an association of the calibration 120 with the image 110. The interface itself 130 can be configured according to the calibration 120 that is applied to the image 110 and the various processing rules embedded into the system 100. For example, the interface 130 can be configured to make certain types of menu options available to the user 140 when the currently active data object 135 includes a particular calibration attribute. The functionalities of the interface 130 will be discussed in more detail below.

The interface 130 can facilitate, allow for, or perform association between a calibration 120 and an image 110. The association may be generated or maintained in any of the ways discussed above, including automatically generating and associating a calibration 120 with an image 110 upon acquisition or import of the image 110. The interface 130 can access and act upon an image 110 that is included in the computer 115. The interface provides functionality for generating, modifying, or selecting a calibration 120 and associating the calibration 120 with the image 110. The interface 130 also allows for the merging of calibrations 120 into one calibration 120.

The interface 130 may provide the user 140 with functions for generating, modifying, or selecting a calibration. The calibration 130 may be selected from a list of calibrations 120. The interface 130 can assist a selection of a calibration 120 by providing a view or a preview of a calibration's 120 curve or data to the user 140. The user 140 can prepare a calibration 120 for an association with an image 110.

The interface 130 provides functionality for associating a particular calibration 120 with a particular image 110. The association can be temporary or lasting. The interface 130 may associate a calibration 120 with an image 110 temporarily for a current application of the calibration 120 to the image 110. The interface 130 can associate a calibration 120 with an image 110 in a permanent (e.g. no inherent expiration) manner such that future applications or functions will automatically apply, or at the least apply as a default calibration 120 for the associated image 110. In many embodiments, the association or relationship is defined through the interface 130 by embedding the calibration 120 into a file or other data object 125 that is associated with the image 110. In some embodiments, the association of the calibration 120 and the image 110 is performed by generating a data object 125 that includes both the calibration 120 and the image 110.

The interface 130 can provide for disassociation of a particular calibration 120 from a particular image 110. The interface 130 may provide functionality to the user 140 for selecting an associated calibration 120 and image 110 and initiating a disassociation of the calibration 120 from the image 110. In some embodiments, the interface 130 removes the calibration 120 from the data object 125 that includes the image 110.

The interface 130 can apply the calibration 120 to an associated image 110 in any of the ways discussed above. The interface 130 can apply the calibration 120 to the image 110 either automatically (in accordance with the processing rules that configure the system 100) or upon an affirmative real-time instruction by the user 140. The interface 130 can be configured to allow the user 140 to instruct the system 100 that an image 110 be converted, calibrated, or otherwise configured according to the associated calibration 120. The interface 130 may allow the user 140 to select to what units or formats an image will be converted. The interface 130 can provide functionality to the user 140 for switching between different units and formats for the display of a converted image 110. The interface 130 can convert the image 110 to the selected units or formats based on an associated calibration 120 that is configured for a conversion of the image 110 to the selected units or formats. In many embodiments of the system 100, the interface 130 accesses the data object 125, such as a file or files that include an associated calibration 120 and image 100, to obtain and apply the calibration 120 to the image 110.

The interface 130 can generate a result of the calibration 120 being applied to the image 110. The result may then be presented or displayed to the user 140. In some embodiments, the interface 130 generates a calibrated image for display. The interface 130 can provide a wide variety of information for display to the user 140, including but not limited to representations of images 110 that have been converted, calibrated, or otherwise configured by the interface 130 or by the computer 115. In many embodiments, the interface 130 can automatically make a subset of menu items available for user interactions while rendering another subset of menu items disabled, based on the calibration 120 applied to an image 110. Other items for display can be selected or modified according to the calibration 120 that is applied to the image 110.

The interface 130 can be configured according to the calibration 120 that is applied to the image 110. The interface 130 may be configured a particular way to provide for displaying a calibrated, converted, or configured image. The configuration of the interface 130 can be performed in an automated manner according to the calibration 120. For example, the interface 130 can be configured a particular way for displaying an image 110 that has been converted to Optical Density (OD) units. The interface 130 can be configured a specific way for displaying an image 110 that has been converted to dosage units such as Gray (GY) units. Similarly, the interface 130 may be configured to display a calibrated image according to any units (e.g. units of measurement) associated with the calibration 120 that was used to calibrate the image 110. The configuration of the interface 130 according to a calibration 120 can be done automatically or without human intervention if the appropriate calibration 120 is associated with the image 110 that is calibrated for display.

The user 140 can use the interface 130 via the access device 135 to interact with the computer 115. In an Internet embodiment of the system 100, the interface 130 is typically a web page that is viewable from a browser in the access device 135. In other embodiments, the interface 130 is likely to be influenced by the operating system and other characteristics of the access device 135. Users 140 can provide system 100 inputs by interacting with the interface 130, and users can also view system 100 outputs through the interface 130.

G. Access Device

The access device 135 allows a user 140 access the system 100 through the interface 130. The access device 135 can be any device that is either: (a) capable of performing the programming logic of the system 100; or (b) communicating with a device that is capable of performing the programming logic of the system 100 (e.g. communicating with the computer 115). Access devices 135 can include desktop computers, laptop computers, mainframe computers, minicomputers, programmable logic devices, embedded computers, hardware devices capable of performing the processing required by the system 100, cell phones, satellite pagers, personal data assistants ("PDAs"), and a wide range of future devices that may not yet currently exist. The access device 135 can also include various peripherals associated with the device such as a terminal, keyboard, mouse, screen, printer, input device, output device, or any other apparatus that can relay data or commands between a user 140 and the interface 130.

H. User

The user 140 can access the system 100 through the access device 135. In many embodiments of the system 100, the user 140 is a human being. In some embodiments of the system 100, the user 140 may be an automated agent, a robot, a neural network, an expert system, an artificial technology device, or some other form of intelligence technology (collectively "intelligence technology"). The system 100 can be implemented in many different ways, giving users 140 a potentially wide variety of different ways to configure the processing performed by the system 100.

II. Subsystem-Level Views

Figure 2A:
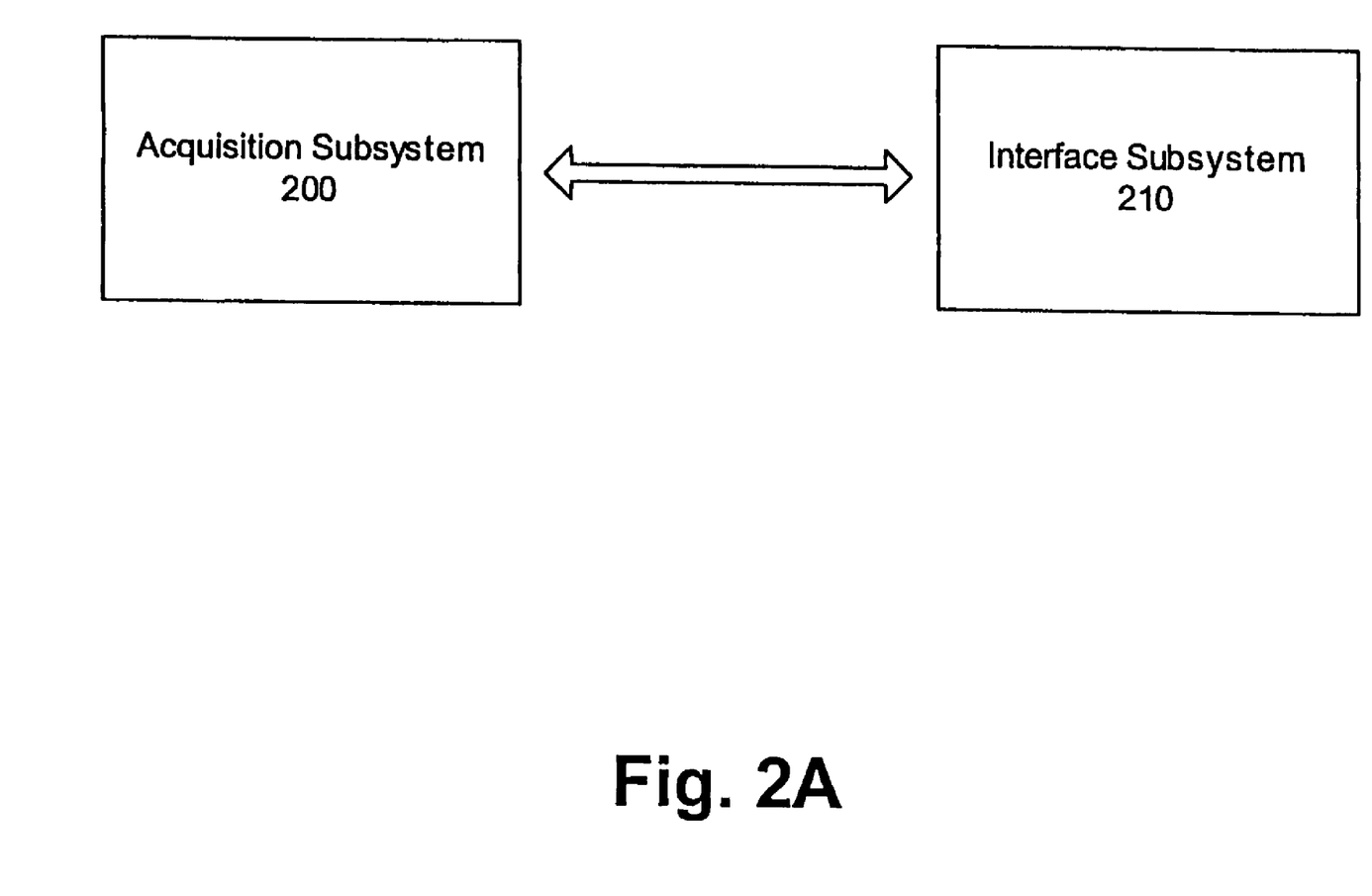
FIG. 2A is a subsystem-level diagram illustrating an example of a system comprising an acquisition subsystem and an interface subsystem.
Figure 2B:
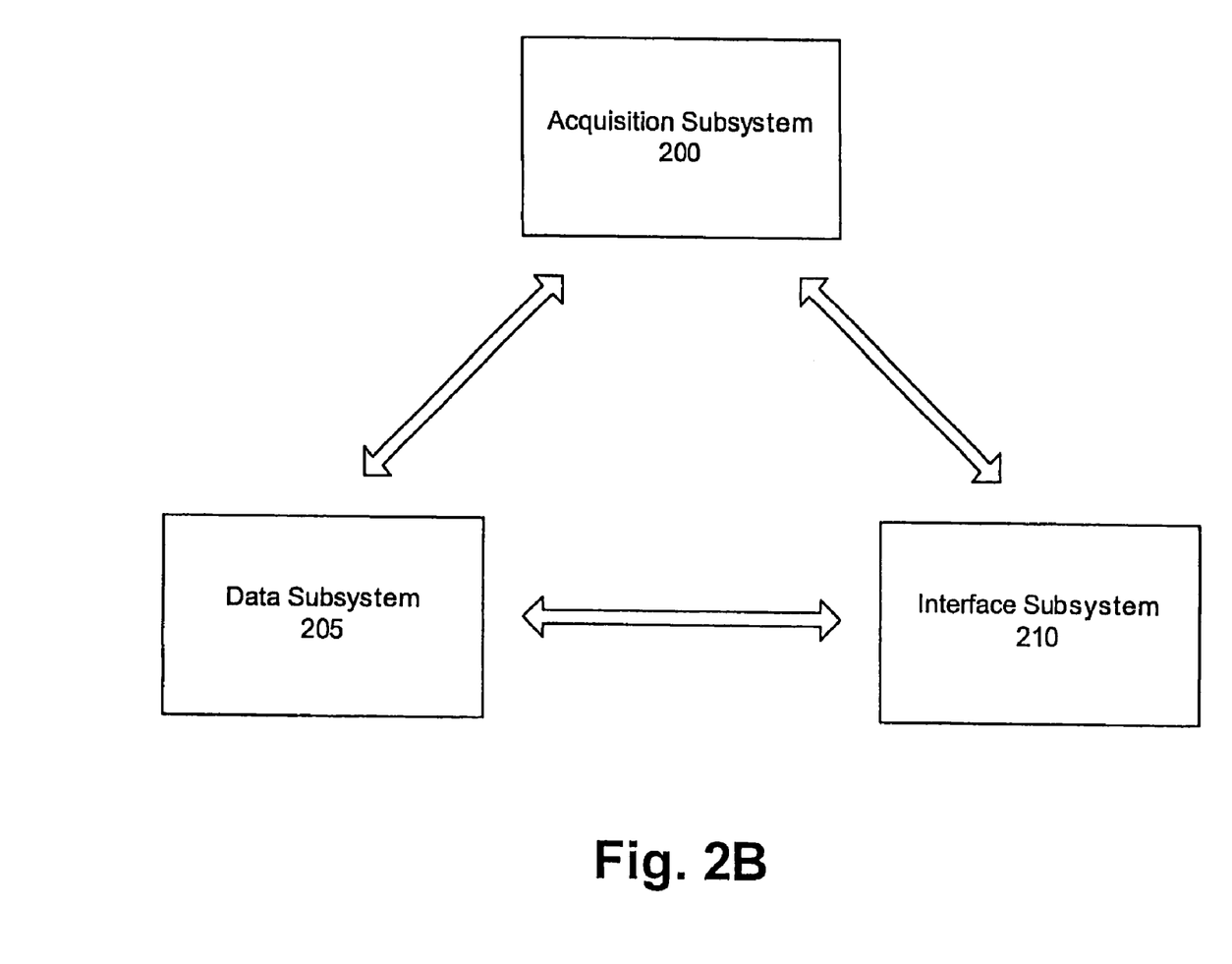
FIG. 2B is a subsystem-level diagram illustrating an example of a system comprising an acquisition subsystem, a data subsystem, and an interface subsystem.

The system 100 can be implemented in the form of various subsystems. A wide variety of different subsystem configurations can be incorporated into the system 100. FIGS. 2A and 2B illustrate different subsystem-level configurations of the system 100. FIG. 2A shows a system 100 made up of two subsystems: an acquisition subsystem 200 and an interface subsystem 210. FIG. 2B illustrates a system 100 made up of three subsystems: the acquisition subsystem 200, a data subsystem 205, and the interface subsystem 210. Interaction between the subsystems 200–210 can include an exchange of data, heuristics, instructions, commands, images, or any other communication helpful for implementation of the system 100.

A. Acquisition Subsystem

The acquisition subsystem 200 allows the system 100 to acquire, import, generate, or otherwise obtain an image 110 or a representation of an image 110. The acquisition subsystem 200 can include any device, application, or process useful for obtaining the image 110, including the acquisition device 105 as described in relation to FIG. 1. The image 110 can be any representation as discussed above in relation to FIG. 1, including a medically related image such as a radiographic image. The acquisition subsystem 200 typically generates an image 110 that is represented in units that are associated with the acquisition subsystem 200 or the process of obtaining the image 110. The acquisition subsystem 200 may generate a calibration 120 upon the generation, importation, or acquisition of the image 110. In many embodiments, the acquisition subsystem 200 generates a file or a group of files that represents an acquired image 110. In some embodiments, the acquisition subsystem 200 generates a separate file to represent a calibration 120 that is related to the acquired image 110.

In the subsystem-level configuration shown in FIG. 2A, the acquisition subsystem 200 can interface with the interface subsystem 210. In the subsystem-level configuration shown in FIG. 2B, the acquisition subsystem 200 can interface with the data subsystem 205. The acquisition subsystem 200 is not a necessary component in all embodiments of the system 100. In some embodiments, a user 140 of the system 100 may be able to control the processes or settings related to the acquisition of an image 110 through other means.

B. Data Subsystem

The data subsystem 205 allows the system 100 to manage data such as representations of calibrations 120 and images 110. The data subsystem 205 may contain various forms of computer-readable mediums, including a database, a non-volatile memory data structure, a volatile memory data structure, and any other computer-readable data structure. In some embodiments, the data subsystem 205 stores images 110 in a computer-readable medium.

The data subsystem 205 can receive images 110 from the acquisition subsystem 200. In embodiments where the acquisition subsystem 200 is not included, the data subsystem 205 can be responsible for acquiring images 110, or images 110 can be received from a different source, including but not limited to, a computer, a computer-readable medium, and the like. In many embodiments, the data subsystem 205 can import images 110 from any type of computer-readable medium. The data subsystem 205 can read or act upon received images 110.

The data subsystem 205 can receive and store one or more calibrations 120. The calibrations can be received and managed in any way discussed above in relation to the data subsystem's 205 processing of images 110. The management of images 110 and calibrations 120 by the data subsystem 205 can include receiving, storing, tracking, changing, deleting, moving, accessing, reading, renaming, or otherwise acting upon the images 110 or the calibrations 120. In some embodiments, images 110 and calibrations 120 are represented in files or other data structures. An image 110 can be represented by one file or by a group of associated files. The data subsystem 205 can organize images 110 and calibrations 120 according to instructions from other subsystems, interfaces, or entities, including instructions from a user 130 of the system 100. In many embodiments, the data subsystem 205 organizes and manages images 110 and calibrations 120 in accordance with instructions received from the interface subsystem 210.

The data subsystem 205 may manage images 110 by associating a particular image 110 with a particular calibration 120. The data subsystem 205 can perform the association in any of the ways discussed above in relation to FIG. 1. In many embodiments, the data subsystem 205 associates the particular calibration 120 and the particular image 110 by generating one or more data object 125 that include one or more calibrations 120 and the image 110. The calibration 120 can be embedded in a header file that is associated with the image 110.

The data subsystem 205 can allow the interface subsystem 210 to access representations of images 110 and calibrations 120. The data subsystem 205 is capable of transmitting the image 110, calibration 120, or copy of the image 110 or calibration 120 to the interface subsystem 210. The data subsystem 205 may receive data objects 125, such as files, that include images, calibrations, and instructions from the interface subsystem 210. The received items can be managed by the data subsystem 205 in any was discussed above.

In some embodiments, the data subsystem 205 allows the interface subsystem 210 to access and process the image 110 and the calibration 120. Once the interface subsystem 210 has processed the image 110 and the calibration 120, it transmits a result to the data subsystem 205. The data subsystem 205 receives the result of the processing. The result can be a file or other type of data object 125 that associates the calibration 120 and the image. The data subsystem 210 incorporate the result in a computer-readable medium for subsequent management and processing activities. In many embodiments, the data subsystem 205 receives the data object 125 which includes the calibration 120 associated embedded within the image 110 that is stored within the data object 125.

The data subsystem 205 can act upon data, including images 110 (image attributes), calibrations 120 (calibration attributes), and data objects 125 (data object attributes) such as files, as instructed by the interface subsystem 210. In accordance with received instructions, the data subsystem 205 can add data structures to a computer-readable medium, modify existing data objects 125, modify calibrations 120 or images 110, delete data structures, or perform any other process helpful to the system 100.

As shown in FIG. 2B, the data subsystem 205 can interface with the acquisition subsystem 200 and the interface subsystem 210. The data subsystem 205 can receive image-related data from the acquisition subsystem 200. In some embodiments, the data subsystem 205 can access data in the acquisition subsystem 200. The data subsystem 205 can transfer image-related data and instructions to the interface subsystem 210 and receive image-related data and instructions from the interface subsystem 210 as discussed above.

C. Interface Subsystem

The interface subsystem 210 allows the user 140 to interact with the system 100. The interface subsystem 210 can include any combination of information technology layers relevant to communications between the user 140 and hardware configurations or software applications. In many embodiments, the interface subsystem 210 includes one or more software applications and one or more display interfaces such as a GUI or web page.

The interface subsystem 210 can receive and process information and instructions from a user 140, including but in no way limited to instructions for modifying image-related information, instructions for modifying a calibration 120, instructions for associating a calibration 120 with an image 110, instructions for embedding a calibration 120 in an image-related file, modifying calibration information such as calibration points or coefficients, and the like. Instructions may also include adding, modifying, copying, renaming, moving, accessing, transmitting, and deleting a calibration 120, image 110, file, or data object 125. In many embodiments, the interface subsystem 210 can receive and process an instruction for embedding a calibration 120 in a header file that is associated with an image 110.

The interface subsystem 210 can provide output to a user 140, including information, prompts, commands, images, and the like. In some embodiments, the interface subsystem 210 provides configurable menu items for display to a user 140. The menu items can be configured according to a calibration 120, general processing rules governing the system 100, or other information or combinations of information. The interface subsystem 210 may provide output to the user 140 for facilitating an association between a particular calibration 120 and a particular image 110. In some embodiments, the interface subsystem 210 assists users 140 in selecting the calibration 120 to be associated with the image 110 by providing a list of calibrations 120 to the user 140. Various heuristics can be used to provide the options most likely to be desirable to a particular user 140, at the top of the list of options. Factors such as the type of input, the history of the particular user 140 with respect to the system 100, a user profile relating to the user 140, general processing rules of the system 100, and different calibration and image attributes can be used by the system 100 in prioritizing the list of options.

The interface subsystem 210 can generate a calibrated image in response to an instruction from a user 140. The interface subsystem generates the calibrated image by applying an associated calibration 120 to an image 110. The generation of the calibrated image can be performed in a wide variety of ways. In some embodiments, the interface subsystem 210 accesses a data object 125 or file that includes an image 110 and an associated calibration 120 and applies the associated calibration 120 to the image 110. The application can be performed automatically and without human interference. One or more calibrations 120 can be embedded in a header associated with an image file to allow for an automatic determination and application of the calibration 120 to the image 110 that is associated with the image file.

The interface subsystem 210 can provide the calibrated image or other formats of a configured image for display to the user 140. The interface subsystem 210 may configure its output according to the applied calibration 120. The output can be configured according to the units or format of the calibrated image. In one embodiment, the interface subsystem 210 automatically configures output for the display of an image that has been calibrated to Optical Density (OD) units or a dosage unit such as Gray (GY) units. The interface subsystem 210 can configure menu items for display in accordance with the calibrations or configurations of images 110.

In some embodiments, the interface subsystem 210 manages images 110 and calibrations 120. FIG. 2A shows a configuration in which the interface subsystem 210 receives images 110 from the acquisition subsystem 200, manages the images 110 and calibrations 120, associates the calibrations 120 with the images 110 as instructed, configures the images 110 according to the associated calibration 120, and provides output related to a calibrated image for display. In some embodiments, the interface subsystem 210 accesses an image 110 and a calibration 120, associates the image 110 and the calibration 120 to each other by embedding the calibration 120 in a file that is associated with the image 110, generates a calibrated image by applying the associated calibration 120 to the image 110, and provides the calibrated image for display.

As shown in FIG. 2B, the interface subsystem 210 is communicatively coupled with the acquisition subsystem 200. The interface subsystem 210 allows a user 140 of the system 100 to influence or control the acquisition subsystem 200. Output may be provided from the acquisition interface 200 to the user 140 by the interface subsystem 210.

III. Input/Output View

Figure 3:
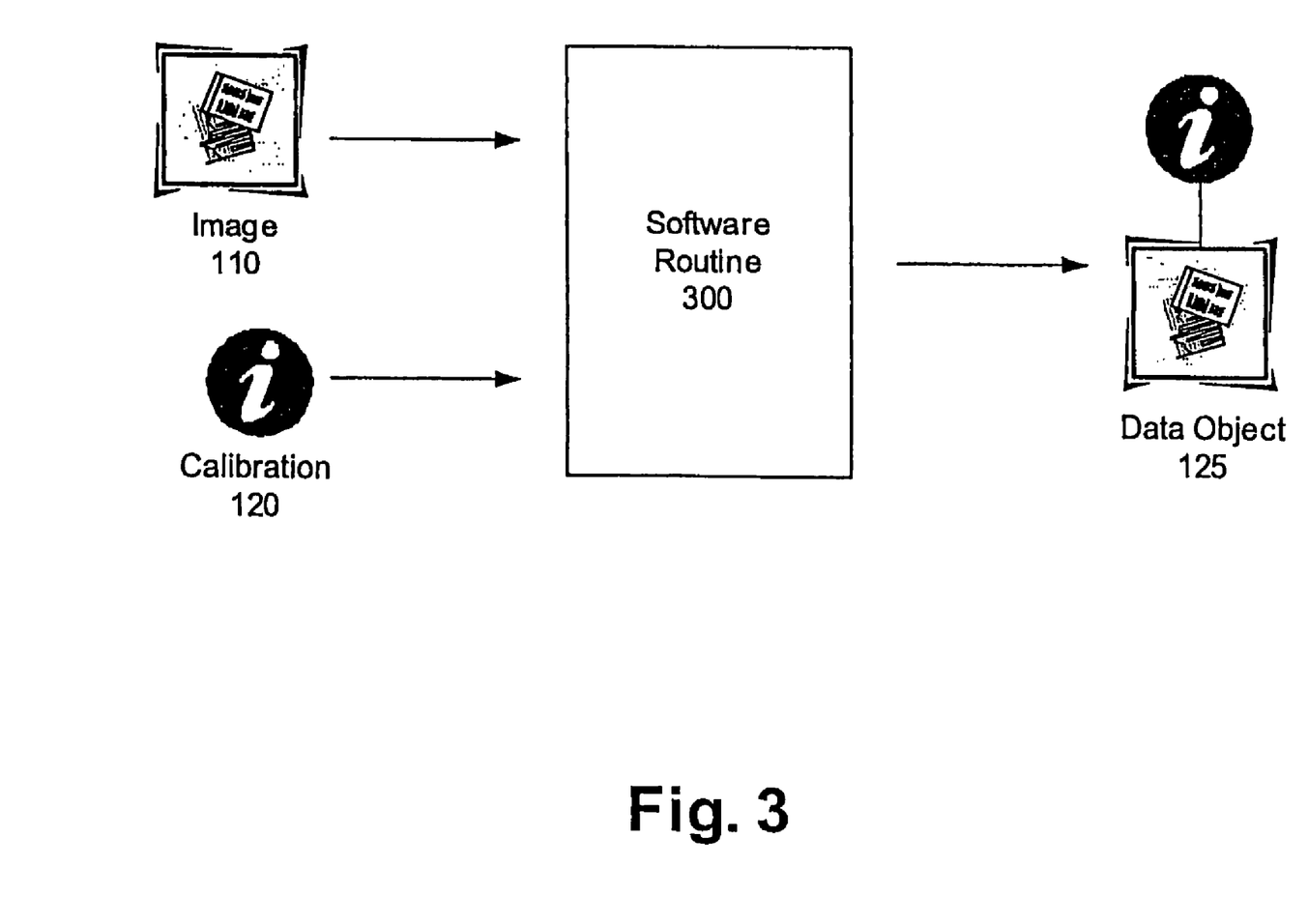
FIG. 3 is a flow diagram illustrating an example of a software routine configured to process input to generate a data object.

FIG. 3 is a diagram illustrating an example of the input and the output of a software routine 300 that can be part of the system 100. The software routine 300 can include any computer-readable application capable of processing images and related data. The software routine 300 can perform any of the functionality discussed above in relation to the subsystems 200–210, the computer 115, and the interface 130. As shown in FIG. 3, the software routine 300 can receive an image 110 and a calibration 120.

The software routine 300 may process the image 110 and the calibration 120 in a wide variety of ways in order to associate the calibration 120 with the image 110, including any of the ways discussed above. The software routine 300 can combine the image 110 and the calibration 120 into one data object 125, such as a file. The calibration 120 can be embedded in a data object 125 or a part of a data object 125 such as a header or a preamble. The data object 125 can comprise any format discussed above in relation to FIG. 1.

In many embodiments, the software routine receives a group of associated files that represent the image 110. The image-related files can be associated in numerous ways, including by sharing a common part of a filename but having different file extensions. The software routine 300 receives the calibration 120 to be associated with the image-related files, and embeds the calibration 120 into one of the image-related files. In several embodiments, multiple calibrations 120 can be associated with the image 110. In some embodiments, the embedded calibration 120 includes information for identifying or locating other calibration data that is not embedded in a file related to the image 110.

FIG. 3 shows a data object 125 to represent an association of the calibration 120 and the image 110. The software routine 300 may provide the data object 125 for communication to any application or device capable of reading or acting upon the data object 125, including a data storage device, the interface 130, the computer 115, or to some type of access device 135. The data object 125 can be accessed by the software routine 300 as instructed. The software routine 300 can generate a calibrated image for display based on the data object's 125 image 110 and associated calibration 120 or calibrations 120.

IV. Process Flow Views

Figure 4A:
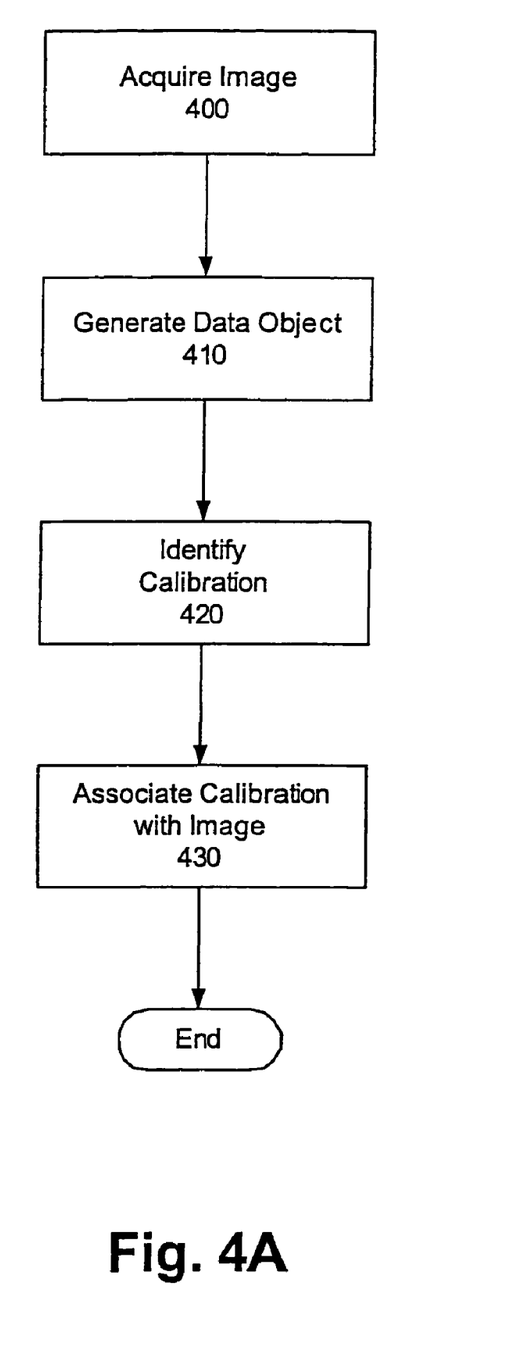
FIG. 4A is a flowchart diagram illustrating an example of a process for associating a calibration with an image.

FIG. 4A is a flowchart diagram illustrating an example of associating one or more calibrations 120 with one or more images 110. As shown in FIG. 4A, the process begins by acquiring an image 110 at step 400. The image 110 can be acquired in any of the ways discussed above, including acquisition by the acquisition device 105. The image 110 can be of any format readable by the computer 115 or the interface 130, as discussed above. In some embodiments of the system 100, the image 110 is a radiographic image related to radiation oncology.

At step 410, a data object 125 is generated. The data object 125 can be of any format discussed above, including a computer-readable file that includes the image 110 or a representation of the image 110. The data object 125 can include any number of files that are associated with the image 110.

At step 420, a calibration 120 is identified. The calibration 120 can be identified in a wide variety of ways, including selection by a user 140 from a list of calibrations 120, definition by a user 140, generation by the acquisition device 105 that acquired the image 110, automatic association according to an identifier associated with the calibration 120, or any other method of identification that can be read or processed by the system 100. In some embodiments, the calibration 120 is identified by the user 140 through the interface 130. The interface 130 allows the user 140 to search for or browse for a calibration 120. In one embodiment, a calibration 120 is automatically associated with an image 110 at the acquisition, importation, or generation of the image 110.

At step 430, the calibration 120 is associated with the image 110. The calibration 120 can be associated with the image 110 in any of the ways discussed above. In an exemplary embodiment, the calibration 120 is embedded in the data object 125 that includes the image 110. In one embodiment, the calibration 120 is embedded in the header portion of a file that is associated with the image 110. The calibration 120 may include information for configuring the image 110, or the calibration 120 may identify or locate information for configuring the image 110.

Figure 4B:
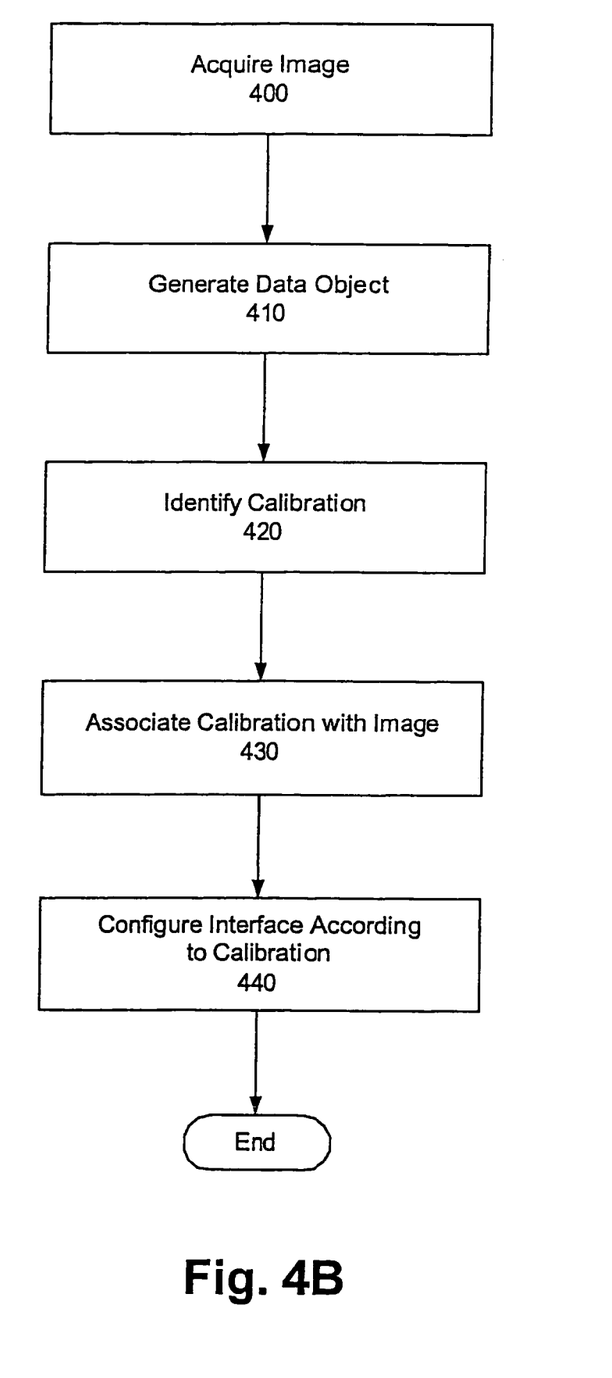
FIG. 4B is a flowchart diagram illustrating an example of a process for configuring an interface according to a calibration of an image.

FIG. 4B is a flow diagram illustrating an example of a process for configuring an interface 130 according to a calibration 120 that is associated with an image 110. Steps 400–430 are the same as discussed in relation to FIG. 4A. At step 440, the interface 130 is configured according to the calibration 120. The interface 130 can be configured in any of the ways discussed above, including adjusting items, parameters, or units for a presentation of a calibrated image. The interface 130 may be configured automatically or without human intervention in accordance with the calibration 120 that has been associated with the image 110. In some embodiments, the interface 130 can be configured to use or to present units that are identified by the calibration 120. In some embodiments, display parameters of the interface 130 are configured according to information associated with the calibration 120. In one embodiment, menu items of the interface 130 are configured for display according to the calibration 120. Any other attribute of the interface 130 can be configured according to the calibration 120 that has been associated with the image 110.

In conclusion, the present methods and systems for associating calibration information with an image and configuring an interface according to the calibration, in its various embodiments, allow for accurate and convenient management of calibration information needed for using images in medical-related applications. Specifically, the present methods and systems provide an interface for using various embodiments of an imaging system, including associating calibration information with images such that the interface can be automatically configured for displaying or otherwise using an image in accordance with the associated calibration information. The present methods and systems allow the appropriate calibration information to be associated with the appropriate images in a manner that prevents the calibration information from being lost, overwritten, or otherwise destroyed. The associated images and calibrations can be more conveniently and accurately transported between computer systems. Medical personnel are better able to manage numerous images and their related calibration information. The chances of incorrectly calibrating an image are reduced, thereby decreasing the chances of a patient suffering a medical misdiagnosis, misadministration, or mistreatment.

The foregoing embodiments were chosen and described in order to illustrate principles of the methods and systems as well as some practical applications. The preceding description enables others skilled in the art to utilize the method and system in various embodiments and with various modifications as are suited to the particular use contemplated. It is intended that the scope of the method and system be defined by the following claims. In accordance with the provisions of the patent statutes, the principles and modes of operation of this invention have been explained and illustrated in exemplary embodiments. However, it must be understood that this invention may be practiced otherwise than is specifically explained and illustrated without departing from its spirit or scope.

What is claimed is:

1. A computer readable medium comprising computer software for:
   generating a data object, wherein said data object includes a radiographic image; and
   associating a calibration with said radiographic image, wherein said calibration is embedded in said data object.

2. The computer readable medium of claim 1, further comprising computer software for obtaining said calibration from said data object.

3. The computer readable medium of claim 1, further comprising computer software for configuring an interface for displaying said radiographic image in accordance with said calibration.

4. The computer readable medium of claim 3, wherein said interface is displayed in accordance with said calibration.

5. The computer readable medium of claim 1, wherein said interface comprises a plurality of menu items, wherein said interface is configured to selectively display a subset of said plurality of menu items.

6. The computer readable medium of claim 1, further comprising computer software for generating a calibrated image based on said radiographic image and said calibration.

7. The computer readable medium of claim 6, further comprising computer software for displaying said calibrated image through an interface in accordance with a plurality of calibration attributes associated with said calibration.

8. The computer readable medium of claim 1, further comprising computer software for converting said radiographic image into a measurement in accordance with said calibration, wherein measurement includes a unit of measurement, and wherein said calibration identifies said unit of measurement.

9. The computer readable medium of claim 8, wherein said unit of measurement includes at least one of an optical density unit and a dosage unit.

10. The computer readable medium of claim 1, further comprising computer software for acquiring said radiographic image with an acquisition device configured for a subsequent transmission of a plurality of said radiographic images into a plurality of said data objects.

11. The computer readable medium of claim 1, wherein said calibration includes a plurality of calibration points and a plurality of coefficients.

12. The computer readable medium of claim 1, wherein said data object includes a header, said header comprising said calibration.

13. The computer readable medium of claim 1, wherein said data object includes a plurality of said calibrations associated with said radiographic image.

14. The computer readable medium of claim 13, wherein said data object includes a header, said header comprising a plurality of calibration attributes associated with said plurality of calibrations.

15. The computer readable medium of claim 1, further comprising computer software for a file, wherein said data object includes at least said file accessible through said interface.

16. The computer readable medium of claim 15, wherein said file includes a header, said header comprising a plurality of calibration attributes.

* * * * *